(12) United States Patent
Reitzmann et al.

(10) Patent No.: US 9,409,160 B2
(45) Date of Patent: Aug. 9, 2016

(54) SHAPED CATALYST BODY FOR FLOW-THROUGH FIXED-BED REACTORS

(75) Inventors: Andreas Reitzmann, Stephanskirchen (DE); Willi Michael Brandstädter, Holzkirchen (DE); Leopold Streifinger, Bruckmühl (DE); Marvin Estenfelder, Ebersberg (DE)

(73) Assignee: SÜD-CHEMIE IP GMBH & CO. KG, München (DE)

( * ) Notice: Subject to any disclaimer, the term of this patent is extended or adjusted under 35 U.S.C. 154(b) by 255 days.

(21) Appl. No.: 13/988,583

(22) PCT Filed: Nov. 22, 2011

(86) PCT No.: PCT/EP2011/070695
§ 371 (c)(1),
(2), (4) Date: Sep. 4, 2013

(87) PCT Pub. No.: WO2012/069481
PCT Pub. Date: May 31, 2012

(65) Prior Publication Data
US 2013/0338378 A1 Dec. 19, 2013

(30) Foreign Application Priority Data
Nov. 22, 2010 (DE) .......................... 10 2010 052 126

(51) Int. Cl.
| | |
|---|---|
| *B01J 35/00* | (2006.01) |
| *B01J 35/02* | (2006.01) |
| *B01J 27/198* | (2006.01) |
| *C07D 307/60* | (2006.01) |
| *C07C 45/33* | (2006.01) |

(Continued)

(52) U.S. Cl.
CPC .............. *B01J 27/198* (2013.01); *B01J 35/026* (2013.01); *C07C 45/33* (2013.01); *C07C 45/35* (2013.01); *C07C 51/215* (2013.01); *C07C 51/252* (2013.01); *C07C 67/00* (2013.01); *C07D 307/60* (2013.01); *Y10T 428/13* (2015.01)

(58) Field of Classification Search
None
See application file for complete search history.

(56) References Cited

U.S. PATENT DOCUMENTS 3,674,680 A * 7/1972 Hoekstra ................ B01J 35/026
208/111.3
3,966,644 A 6/1976 Gustafson
(Continued)

FOREIGN PATENT DOCUMENTS

| CN | 1050181 | 3/1991 |
| DE | 3141942 | 8/1982 |

(Continued)

OTHER PUBLICATIONS

International Search Report for PCT/EP2011/070695 of Feb. 6, 2012.
(Continued)

*Primary Examiner* — Colin W Slifka
(74) *Attorney, Agent, or Firm* — Anthony A. Bisulca

(57) ABSTRACT

The invention relates to a shaped catalyst body for the catalytic conversion of organic and inorganic components in fixed-bed reactors, wherein the shaped catalyst body is formed as cylinder with a base, a cylinder surface, a cylinder axis and at least one continuous opening running parallel to the cylinder axis, and the base of the cylinder has at least four corners.

21 Claims, 2 Drawing Sheets

Figure 1A:
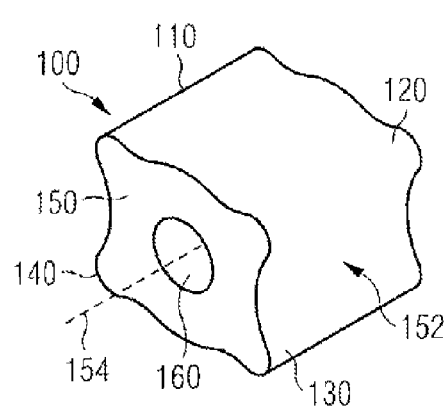

(51) Int. Cl.
*C07C 45/35* (2006.01)
*C07C 51/215* (2006.01)
*C07C 51/25* (2006.01)
*C07C 67/00* (2006.01)

(56) References Cited

U.S. PATENT DOCUMENTS

| | | | |
|---|---|---|---|
| 4,328,130 A | 5/1982 | Kyan | |
| 4,370,492 A | 1/1983 | Wunder et al. | |
| 4,441,990 A * | 4/1984 | Huang | B01J 29/40 208/111.15 |
| 5,072,052 A | 12/1991 | Boeck et al. | |
| 5,082,819 A | 1/1992 | Boeck et al. | |
| 5,097,091 A | 3/1992 | Kremer et al. | |
| 5,147,526 A | 9/1992 | Kukes et al. | |
| 5,364,514 A | 11/1994 | Sanborn et al. | |
| 6,175,046 B1 | 1/2001 | Enomoto et al. | |
| 6,518,220 B2 | 2/2003 | Walsdorff et al. | |
| 6,624,114 B1 | 9/2003 | Eberle et al. | |
| 6,812,351 B2 | 11/2004 | Weiguny et al. | |
| 7,169,736 B2 | 1/2007 | Petrolli et al. | |
| 8,048,820 B2 | 11/2011 | Brandstadter et al. | |
| 2008/0277315 A1 | 11/2008 | Ringer et al. | |
| 2011/0105790 A1 | 5/2011 | Hagemeyer et al. | |
| 2011/0257414 A1 | 10/2011 | Dobner et al. | |
| 2013/0323163 A1 | 12/2013 | Sauerbeck et al. | |
| 2014/0020413 A1 | 1/2014 | Sauerbeck et al. | |

FOREIGN PATENT DOCUMENTS

| | | |
|---|---|---|
| DE | 39 35 073 A1 | 4/1991 |
| DE | 3930533 | 5/1991 |
| DE | 100 11 307 | 9/2001 |
| DE | 102 11 447 | 10/2003 |
| EP | 0 003 818 | 9/1979 |
| EP | 0 004 079 | 9/1979 |
| EP | 0 220 933 | 5/1987 |
| EP | 0579234 | 1/1994 |
| EP | 1 108 470 | 6/2001 |
| EP | 1127618 | 8/2001 |
| WO | WO 0158590 | 8/2001 |
| WO | WO 2006/114320 | 11/2006 |
| WO | WO 2007/051602 | 5/2007 |
| WO | WO 2009121626 | 10/2009 |
| WO | WO 2010/029325 | 3/2010 |
| WO | WO 2010/072721 | 7/2010 |

OTHER PUBLICATIONS

International Preliminary Report on Patentability for PCT/EP2011/070695, mailed May 22, 2013.
English abstract for DE 102 11 447, dated Oct. 2, 2003.

* cited by examiner

SHAPED CATALYST BODY FOR FLOW-THROUGH FIXED-BED REACTORS

The present invention relates to a shaped catalyst body for the catalytic conversion of organic and inorganic compounds in fixed-bed reactors.

Maleic anhydride is a chemical intermediate product of considerable commercial interest. It is used alone or also in combination with other acids for example in the production of alkyd and polyester resins. In addition, it also represents an intermediate product for chemical synthesis with multiple uses, for example for the synthesis of gamma-butyrolactone, tetrahydrofuran and 1,4-butanediol, which in turn for their part are used as solvents or further processed to polymers, such as for example polytetrahydrofuran or polyvinylpyrrolidone.

As a rule, maleic anhydride (MA) is produced by partial oxidation of hydrocarbons in the gas phase with molecular oxygen or with a molecular oxygen-containing gas in the presence of a vanadium phosphorus oxide catalyst (VPO). Various oxidation catalysts, various shaped catalyst bodies and various procedures are applied. In general, the oxidation catalysts contain mixed oxides of vanadium and phosphorus, wherein oxidation catalysts with vanadium in a valency of from +3.8 to +4.8 have proved particularly suitable for producing maleic anhydride from saturated hydrocarbons with at least four carbon atoms in a straight chain. In addition to vanadium, phosphorus and oxygen, the VPO catalysts can also contain promoters such as for example metals, which can be present in the form of their oxides in the oxidation catalyst.

To produce e.g. maleic anhydride by heterogeneous catalytic gas-phase oxidation of hydrocarbons, shaped catalyst bodies containing vanadium, phosphorus and oxygen with geometries different from one another are used.

EP1261424 B1 relates to a catalyst for producing maleic anhydride by heterogeneous catalytic gas-phase oxidation of a hydrocarbon with at least 4 carbon atoms. This catalyst contains a catalytically active mass of a vanadium phosphorus mixed oxide and has a substantially hollow cylindrical structure. The hollow cylinder is formed such that the ratio of the height to the diameter of the passage is at most 1.5 and the ratio of the geometric surface area to the geometric volume of the shaped body is at least 2 $mm^{-1}$.

EP0552287 B1 describes a shaped catalyst body for producing maleic anhydride, wherein the shaped body comprises a solid geometric shape with at least one void space arranged in the external surface. The shaped body is formed from mixed oxides of vanadium and phosphorus and has a geometric volume of from 30% to 67% of the geometric volume which the solid shaped body, free of void space, occupies, wherein the ratio of the geometric surface area of the shaped body to the geometric volume of the shaped body is at least 20 $cm^{-1}$.

WO2007051602 A1 relates to a shaped catalyst body for producing maleic anhydride, containing mixed oxides of vanadium and of phosphorus as catalyst component. In order to further develop a shaped catalyst body according to the preamble such that it has improved properties, it is proposed that the geometric base body enclosing the shaped catalyst body is a prism with a first and a second triangular surface and the shaped catalyst body is provided with three continuous openings which extend from a first surface of the shaped body, which spans the first triangular surface of the prism, to a second surface of the shaped body, which spans the second triangular surface of the prism.

WO0158590 A1 relates to a Pd/Ag support catalyst, wherein the shaped body has a trilobal geometry.

DE10011307 A1 claims a VPO hollow cylinder for producing MA with specific geometric dimensions which in principle result in relatively flat hollow cylinders with a relatively large inner hole.

In DE10211447 A1, a VPO catalyst for the selective oxidation of hydrocarbons with at least 4 C atoms is claimed which essentially has a hollow cylindrical structure and the tablet density of which is below a value calculated according to an empirical formula.

In EP1127618 A1, shaped catalysts in the form of hollow cylinders are disclosed in which the end-surfaces are rounded at the outer edge and also at the edge of the internal hole.

In EP0004079, a catalyst for producing vinyl acetate in the gas phase is described which contains noble metals of the 8th sub-group, gold, alkaline, alkaline-earth and cadmium compounds on a support which has a star-shaped cross-section.

DE3141942 C2 relates to a cylindrical shaped catalyst body which has the structure of a circular cylinder with several longitudinal channels which have a specific depth and width.

EP220933 A1 describes four-leaved-clover-shaped catalytic extrudates for conversions of hydrocarbons in fixed-bed reactors (quadrulobes).

In EP1108470 B1, catalysts are described with an active catalyst material on an inert support in the shape of rings which have one or more notches on the upper and/or lower flat face of the ring.

WO2009121626 A1 relates to a process for producing a nanocrystalline molybdenum mixed oxide, and the use of the molybdenum mixed oxide in a catalyst for chemical conversions, e.g. in a supported catalyst for converting acrolein to acrylic acid.

It is the object of the present invention to create a shaped catalyst body for the catalytic conversion of organic and inorganic compounds which is improved compared with the state of the art and in particular allows catalytic conversions of organic and inorganic compounds with a higher selectivity and with a higher productivity.

Feedstocks of shaped catalyst bodies typically result in a pressure loss when a fluid (gas/liquid) flows through them. As a result, in fixed-bed reactors through which fluid flows a degree of reactor inlet pressure must be applied in order to allow the reaction mixture to flow through fixed-bed reactors. The greater the pressure loss of the feedstock, the higher the reactor inlet pressure that must be selected. This means that a higher compressor power must be used in order to allow the fluid to flow through the feedstock. Higher compressor power means an increase in operating costs. The development of shaped bodies which have a low pressure loss is therefore very desirable.

In one embodiment of the invention, a shaped catalyst body for the catalytic conversion of organic and inorganic compounds in fixed-bed reactors is provided, wherein the shaped catalyst body is formed as cylinder with a base, a cylinder surface, a cylinder axis and at least one continuous opening running parallel to the cylinder axis, and the base of the cylinder has at least four corners. The corners can serve as spacers vis-à-vis adjacent shaped bodies.

The shaped catalyst body according to embodiments described here, also called shaped body here, has a specific geometry, e.g. for full catalysts which, when a majority of the shaped catalyst bodies are introduced as feedstock into tubular reactors, result in a minimizing of the pressure loss when the reactor is flowed through. As a result of the smaller loss in pressure, higher flow rates and space velocities (GHSV=total volume flow/reactor volume) can be achieved for the same reactor inlet pressure using feedstocks of the shaped catalyst bodies according to embodiments than with feedstocks comprising bodies with higher pressure loss. Higher space-time yields (volume flow product/reactor volume) and catalyst productivities (mass flow product/catalyst mass) of valuable product can thereby be achieved. A greater quantity of valuable product can be produced using the shaped catalyst body of embodiments per expenditure of energy (pressure energy) than with rings. Compared with rings or hollow cylinders, the shaped catalyst bodies of embodiments described here surprisingly also have a higher mechanical stability. The use of the shaped catalyst bodies according to the invention, also called shaped bodies here, is described below using the example of partial oxidation of butane to maleic anhydride in the gas phase in fixed-bed reactors, but is not limited thereto. The shaped bodies can be used in all flow-through fixed-bed reactors which contain feedstocks of shaped catalyst bodies and are used for the catalytic conversion of organic and inorganic components in gas and liquid phase.

The shaped catalyst bodies of embodiments described here are characterized by an increased specific activity per g/catalyst and an increased selectivity. In turn, an increased productivity can thereby be obtained. The term "productivity" denotes the mass flow of for example MA per catalyst mass. An increased productivity means that more product, e.g. maleic anhydride (MA), can be synthesized per unit of time in an existing production plant.

Moreover, for a given maximum pressure loss of a catalyst feedstock, space velocities (GHSV=volume flow/catalyst volume) at least 20% higher can be applied compared with known shaped body geometries such as e.g. spheres, solid cylindrical tablets or extrudates. If e.g. a maximum GHSV of $2500\ h^{-1}$ is possible with one of the previously known shaped bodies, space velocities of at least $3000\ h^{-1}$ can be achieved for the same pressure loss using the shaped catalyst bodies according to embodiments. On the other hand, due to the specifically smaller pressure build-up it is also possible to realize a given throughput, e.g. GHSV of $2500\ h^{-1}$, for a smaller pressure loss than with conventional shaped bodies. As a result, a smaller fan capacity must be used, which leads to a saving of energy costs.

Furthermore, the shaped bodies according to embodiments surprisingly make possible a shaping with lower pressing and/or ejection forces than e.g. annular shaped bodies. This reduces the mechanical wear on the tools that are used to shape the shaped bodies. Tools used to produce shaped bodies, for example tabletting tools with punches and female moulds, experience strong mechanical stresses. The greater the mechanical stress, the greater the wear on the tools, which shortens the life of the tools. These undesired effects can be avoided with shaped bodies according to the invention.

Furthermore, surprisingly the maximum temperature in the catalyst bed (hot spot temperature) is lower with shaped catalyst bodies of embodiments than with known shaped catalyst bodies. This can be attributed to the fact that an improved heat removal and heat distribution is achieved by the geometry of shaped catalyst bodies according to the invention in catalyst beds.

Furthermore, the shaped catalyst bodies of embodiments described here have a high mechanical stability, with the result that for example when the shaped bodies are being transported and a multitube fixed-bed reactor is being filled with the shaped catalyst bodies, there is essentially no damage to the shaped bodies. Moreover, according to some embodiments shaped catalyst bodies have rounded boundary lines. A simple and reproducible filling procedure for a reactor with low formation of voids is thereby made possible.

In addition, shaped catalyst bodies according to embodiments have relatively short diffusion paths. The short diffusion paths result in a high degree of pore utilization, with the result that a lower catalyst mass can be used to achieve a desired hydrocarbon conversion, as well as a higher selectivity for example of MA, as the total oxidation of MA to CO and $CO_2$ is suppressed.

Furthermore, shaped catalyst bodies according to embodiments combine lower densities with at least equal shaped body stability. This results in higher pore volumes and larger pore dimensions, which accelerates the diffusion of the reactants and products in the catalyst body. The improved diffusion leads to higher degrees of pore utilization, with the result that a lower catalyst mass can be used to achieve a desired hydrocarbon conversion, as well as to a higher selectivity for example of MA, as the total oxidation of MA to CO and $CO_2$ is suppressed.

With the shaped catalyst body, according to one embodiment a geometric base body enclosing the shaped catalyst body can be a prism which has a prism base with a length and a width, wherein the length is greater than the width. For example, the prism can be a cuboid.

In another embodiment, a recess can be provided in the cylinder surface between two adjacent corners in the shaped catalyst body. Alternatively or in addition, a protrusion can be provided in the cylinder surface between two adjacent corners. The shaped catalyst body can comprise two recesses arranged opposite each other and/or two protrusions arranged opposite each other. The protrusions can also be considered further corners of the shaped catalyst body.

According to one embodiment, the shaped catalyst body has an opening running parallel to the cylinder axis. In a further embodiment, the shaped catalyst body has four corners.

In the case of the shaped catalyst body of embodiments described here, at least one element selected from the corners, the recess, the recesses, the protrusion and the protrusions can be rounded. In this case, the corners, the recess(es) and the protrusion(s) are limited by circular arcs. Rounded corners of the shaped catalyst body are also called lobes here. As a rule, known prismatic shaped catalyst bodies have a relatively low stability along their longitudinal edges, with the result that for example when a reactor is being filled with the corresponding shaped catalyst bodies spalling can occur in the region of the longitudinal edges. This is avoided by the rounded elements of the shaped catalyst body of the embodiments described here.

According to one embodiment, simple to realize in production terms and thus cost-favourable, of the shaped catalyst body the continuous openings have a circular or oval cross-section. In one embodiment, the corners of the shaped catalyst body are enclosed by prism corners of the prism base of the geometric base body enclosing the shaped catalyst body. Two corners can define the length of the prism base and/or two corners define the width of the prism base. According to a further embodiment, the protrusion or protrusions can be provided between corners that define the length, and/or the recess or recesses provided between corners that define the width.

For example, when producing maleic anhydride by heterogeneous catalytic gas-phase oxidation of hydrocarbons, pressure losses occur in the reactor bed which have a disadvantageous effect on the gas throughput and thus on the product capacity, or require increased fan capacity. In order to keep the pressure loss in the reactor as small as possible and in order to achieve the shortest possible diffusion paths within the shaped catalyst body, according to a particularly preferred embodiment the continuous openings of the shaped catalyst body have a diameter of from approximately 0.5 mm to 3 mm, preferably 1 mm to 2.5 mm.

In order to positively influence the flow of the gas mixture passing through the catalyst bed when producing maleic anhydride by heterogeneous catalytic gas-phase oxidation, i.e. to shorten the diffusion path while maintaining sufficient stability, it can be provided in preferred production terms that the continuous openings have the same diameter. According to an alternative embodiment, it can be provided that the continuous openings have a diameter different from one another.

One factor that jointly determines the filling density of shaped catalyst bodies in a reactor is the geometry of the shaped catalyst bodies. In order to influence the filling density and thus influence the space velocities of the gas passing through the catalyst bed, it can be provided according to a further embodiment of the shaped catalyst body that at least two of the at least four rounded corners, e.g. the lobes, have the same external diameter. According to an alternative embodiment, at least two or all lobes or corners have the same or a different external diameter.

Furthermore, the filling density of a reactor charged with shaped catalyst bodies depends on the size of the corresponding shaped bodies. In order to achieve suitable space velocities of the hydrocarbon- and oxygen-containing gas mixture when producing maleic anhydride by heterogeneous catalytic gas-phase oxidation, the shaped bodies preferably have a height of from approximately 2 to 20 mm, in particular from 3 to 10 mm, preferably 3 to 6 mm. The height is the dimension of the shaped catalyst body parallel to the cylinder axis.

According to a further embodiment, the corners of the shaped catalyst body are rounded, they each have a centre of gravity, and/or at least two of the corners are different from each other. In each case, the centre of gravity can be approximately 1.5 to 5 mm, preferably 2.5 to 4 mm from the cylinder axis. The rounded corners can have a diameter of the rounding in the range of from approximately 1 to 2 mm. The radius of the circular arc formed in each case by the rounded corners can be in the range of from approximately 0.5 to 2.5 mm. The radius of the circular arc formed in each case by the rounded protrusions can be in the range of from approximately 2 to 3.5 mm. Furthermore, the radius of the circular arc formed in each case by the rounded recesses can be in the range of from approximately 1 to 9 mm.

In the case of another embodiment, the corners of the shaped catalyst body can be arranged in the base such that the angle between the perpendicular on a straight line through the centres of gravity of two corners that define the width of the prism base and a straight line through the centre of gravity of these corners and through the cylinder axis is approximately 10° to 75°, preferably 25° to 60°.

Furthermore, in one embodiment of the shaped catalyst body the external diameter of the cylinder or the distance between two opposing recesses can be approximately 3 to 10 mm, preferably 5 to 8 mm. The diameter of the opening or openings of the shaped catalyst body can be 0.5 to 4 mm, preferably 1 to 3 mm.

As explained above, in examples of embodiments the enclosing geometric base body is a cuboid. In further embodiments, the ratio of the volume of the shaped body according to the invention to the volume of the surrounding cuboid can be greater than 80% without taking the opening(s) into account, i.e. including the volume of the opening(s), and greater than 70% taking the opening(s) into account, i.e. excluding the volume of the opening(s).

In embodiments, the shaped body according to the invention has a geometric surface area of from approximately 0.15 $cm^2$ to 5 $cm^2$, preferably 0.5 $cm^2$ to 4 $cm^2$, particularly preferably 1 $cm^2$ to 3.5 $cm^2$, in particular 1.5 $cm^2$ to 3 $cm^2$.

According to a further preferred embodiment of the shaped catalyst body, the ratio of the geometric surface area of the shaped body to the volume of the shaped body is approximately 1 to 1.8 $mm^{-1}$, and the ratio of the geometric surface area of the shaped body to its volume is preferably at least 1.2 $mm^{-1}$ or between 1.2 and 1.8 $mm^{-1}$, wherein the volume less the volume of the opening(s) was used as volume of the shaped body, i.e. taking the opening(s) into account.

According to one embodiment of the shaped catalyst body, the bulk density of the shaped catalyst body is less than 0.75 kg/l, preferably between 0.45 and 0.7 kg/l.

The production of maleic anhydride by heterogeneous catalytic gas-phase oxidation as an example is usually carried out in so-called multitube reactors in which shaped catalyst bodies are layered on top of one another in vertically aligned tubes. Accordingly, a shaped catalyst body must be able to withstand the weight of the shaped bodies lying above it. According to a further preferred embodiment of the shaped body, an average unidirectional lateral compressive strength is greater than 28 N, preferably between 30 and 60 N, and/or a different average unidirectional lateral compressive strength, i.e. the lateral compressive strength in a different direction, greater than 70 N, preferably between 80 and 240 N.

The BET surface area of the shaped catalyst body according to the invention can be approximately 10 to 300 $m^2/g$, preferably 12 to 80 $m^2/g$, particularly preferably 15-50 $m^2/g$. The BET surface area is determined using the single-point method by adsorption of nitrogen according to DIN 66132.

It can further be preferred that the integral pore volume (determined according to DIN 66133 (Hg porosimetry)) is >100, preferably >180 $mm^3/g$.

The shaped catalyst bodies according to embodiments can contain the catalytically active component(s), here also called catalyst component(s), for example in pure, undiluted form as so-called "full catalysts" or diluted with a preferably oxidic support material as support catalyst or as so-called supported "catalyst".

In so-called heterogeneous catalysis a distinction is typically drawn between two types of (solid) catalyst (J. Weitkamp and R. Glaser in: Winnacker/Kuchler "Chemische Technik: Prozesse and Produkte", vol. 1, chapter 5, Wiley-VCH, 2004):

Firstly, there are so-called "supported catalysts", also called coating catalysts, by which are meant solid catalysts that are produced by coating a (usually non-porous) support body with a porous layer containing the actual catalytically active species.

In contrast, in the so-called "support catalysts" the catalytically active species, e.g. noble metals, such as Pd, Pt, Au, Ag etc., is applied dispersely by impregnation methods as solution of a (reducible) compound of this species to a porous support, such as e.g. $SiO_2$, $Al_2O_3$, $TiO_2$, $ZrO_2$, etc. In the case of the support catalysts produced by the impregnation method, there are mostly physicochemical interactions between support and active species which have a decisive influence on the catalytic process.

In the case of the supported catalysts, the catalyst body serves merely to provide shape ("structural support"). In contrast to support catalysts, in which the active elements are distributed dispersely in the porous support—optionally also in an outer shell arranged on the support (=shell catalyst)—in the case of the supported catalyst the typically non-porous support body is enclosed by a layer containing the active species.

Suitable support materials for the supported catalysts are for example aluminium oxide, silicon dioxide, aluminium silicates, zirconium dioxide, titanium dioxide or mixtures thereof. The content of the catalyst component in the shaped catalyst body is preferably approximately 3 to 50 wt.-% relative to the total weight of the shaped catalyst body. In the case of a supported catalyst, the content of the catalyst component in the shaped catalyst body is 3-50 wt.-%, preferably 5-30 wt.-% relative to the total weight of the shaped catalyst body.

The shaped catalyst body of the embodiments can be formed as full catalyst, as supported catalyst or as support catalyst. The shaped catalyst body can comprise, as catalytically active component, oxides of vanadium and phosphorus, e.g. for producing maleic anhydride from n-butane. Other catalytically active components of the shaped catalyst body can be one or more metals of the sub-groups of the periodic table, one or more metal oxides or mixed metal oxides of metals of the sub-groups of the periodic table. For example, the shaped body can comprise Bi, Mo, Fe, Ni, W, Sb, Co, Mg, Zn, Si, K, Cs, their oxides and/or their mixed oxides as catalytically active components, for example for converting propene to acrolein. The shaped body can also comprise Mo, V, W, Cu, Sb, their oxides and/or their mixed oxides as catalytically active components, for example for converting acrolein to acrylic acid. The shaped body can also contain e.g. Mo, V, Te, Nb, Sb, for e.g. converting propane to acrylic acid. The shaped body of embodiments can also comprise one or more noble metals, such as Pd, Pt, Au and/or Ag as catalytically active components, e.g. for producing vinyl acetate from ethene in the presence of acetic acid.

In embodiments, the shaped catalyst body can contain as further catalytically active component a promoter which is selected from metals of the periodic table of the elements. According to a preferred embodiment of the shaped catalyst body, the catalyst component contains oxides of vanadium and phosphorus and corresponds to the general formula

$$VP_xO_yM_z$$

wherein M is at least one promoter, x represents a number from 0.1 to 3, y is a number matched to one of the valencies of V, P and M and z represents a number from 0 to 1.5.

As already stated above, the promoter can be selected from the metals. Preferably, the promoter is selected from chromium, nickel, magnesium, aluminium, silicon, tungsten, niobium, antimony and/or caesium.

Depending on the procedure, it can be preferred to also use promoter elements other than those mentioned above. In the case of a corresponding procedure, it can therefore be preferred if the promoter is further selected from lithium, zinc, iron, bismuth, tellurium, silver, molybdenum and/or zirconium.

It is advantageous if the proportion of promoter in the form of an oxide or in the form of a compound which can be converted into an oxide, is 0.005 wt.-% to 5 wt.-%, relative to the total weight of the shaped body.

Adjuvants, such as for example tabletting aids or pore formers, can also be added to the shaped catalyst body. Tabletting aids are generally added if the shaped catalyst body is shaped using tabletting. Tabletting aids are usually catalytically inert and improve the tabletting properties of the so-called catalyst precursor powder, for example by increasing the slip and/or flow properties. A particularly suitable tabletting aid is for example graphite. The added tabletting aids can remain in the activated catalyst and are generally present in an order of from 1 to 5 wt.-% in the shaped catalyst body relative to the total weight of the shaped catalyst body.

In addition, the shaped catalyst body can contain pore formers. Pore formers are substances that are used for the targeted setting of the pore structure in the meso- and macropore range. As a rule, these are compounds containing carbon, hydrogen, oxygen and/or nitrogen which are added to the catalyst precursor powder before shaping and decompose or evaporate during the subsequent activation of the shaped catalyst body for example by calcining and thus largely leave the resulting shaped body, producing pores as they do so.

The shaped catalyst body of embodiments can be used for a partial oxidation reaction, for a partial oxidation reaction of one or more hydrocarbons, for producing maleic anhydride from hydrocarbon, for producing vinyl acetate monomer by oxidation of ethene in the presence of acetic acid, or for oxidizing propene or propane to acrolein and/or acrylic acid. One embodiment relates to the use of the shaped catalyst body according to the above embodiments for partial oxidation reactions, for partial oxidation reactions of hydrocarbons or for producing maleic anhydride from hydrocarbons. With such a use, n-butane can be used as hydrocarbon. A use of embodiments for producing maleic anhydride from hydrocarbons is described below, without the invention being limited thereto.

Non-aromatic hydrocarbons with 4 to 10 carbon atoms can be used as hydrocarbons. The hydrocarbon must contain not less than 4 carbon atoms in one straight chain or in one ring. The hydrocarbon n-butane is particularly suitable. Apart from n-butane, pentanes, hexanes, heptanes, octanes, nonanes, decanes or mixtures of any of these compounds with or without n-butane are also suitable, provided they contain at least 4 carbon atoms in a straight chain.

Unsaturated hydrocarbons can likewise be used for conversion to maleic anhydride. Suitable unsaturated hydrocarbons are for example butenes (1-butene and 2-butene), 1,3-butadiene, pentenes, hexenes, heptenes, octenes, nonenes, decenes as well as mixtures of any of these compounds provided that they contain at least 4 carbon atoms in a straight chain. Equally suitable are substituted and unsubstituted furans, e.g. tetrahydrofuran, in addition aromatic compounds, for example benzene and its derivatives.

The shaped catalyst body according to embodiments described here can be produced for example as described in WO 97/12674, wherein the shaping is carried out according to the geometry of the embodiments.

The essential steps of a possible production of a VPO shaped catalyst body with formation of a catalyst precursor powder, shaping and subsequent activation are described briefly below by way of example:

Reacting a pentavalent vanadium compound (for example $V_2O_5$) with a reducing solvent (for example isobutanol) in the presence of a pentavalent phosphorus compound (for example o-phosphoric acid or a different phosphoric acid such as pyrophosphoric acids and/or their mixtures etc.) and optionally a promoter. The above-named reaction can optionally be carried out in the presence of a support material which is present for example in powder form and is dispersed in the solvent.

Producing the formed catalyst precursor containing vanadium, phosphorus and oxygen, for example by means of filtration, evaporation, decanting or centrifuging.

Drying and optionally calcining the catalyst precursor. Optionally, powdered support material and/or a pore former can be mixed in with the dried catalyst precursor. The drying can be carried out for example in vacuum under protective gas or with an excess of oxygen.

Shaping by conversion to the geometry according to embodiments described here. Before shaping, a tabletting aid can be added to the dried catalyst precursor.

Activating the catalyst precursor containing vanadium, phosphorus and oxygen and optionally promoter by heating in an atmosphere that can contain oxygen, nitrogen, noble gases, carbon dioxide, hydrocarbons, carbon monoxide and/or steam or mixtures thereof. The mechanical and/or catalytic properties of the shaped catalyst body can be determined by selection of temperature, heating rate, treatment duration and gas atmosphere.

The shaped catalyst body can be produced for example by first mixing the dried catalyst precursor powder with a binder or with a slip additive. The shaped body is then produced for example in a tablet press with a rotary table at the periphery of which several openings with a corresponding cross-section, for example a four-lobed cross-section, are disposed. The mixture is filled into this opening (female moulds), and is held from below by a punch by means of which, when the rotary table is rotated, for example three pins that are located at the points of the openings to be produced are pushed upwards. As the rotary table rotates further, a punch with a corresponding cross-section engages, provided with openings which the pins penetrate when the upper punch is depressed. As the rotary table rotates further, the compressed shaped bodies are pressed out of the female moulds after the lower punch has been withdrawn and the upper punch pushed further. The thus-formed shaped catalyst body is then activated, e.g. by calcining.

Further features and advantages result from the following description of embodiments, the figures and the dependent claims.

Figure 1B:
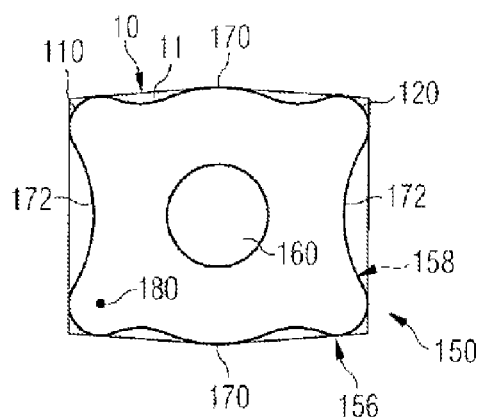
Figure 2A:
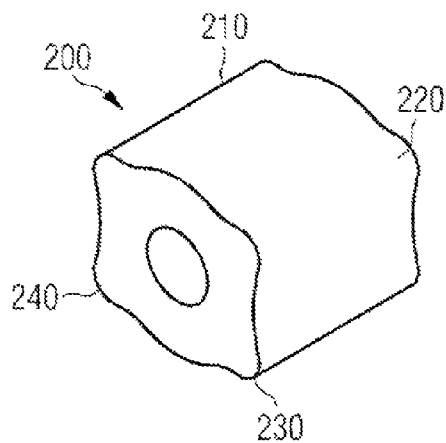
Figure 2B:
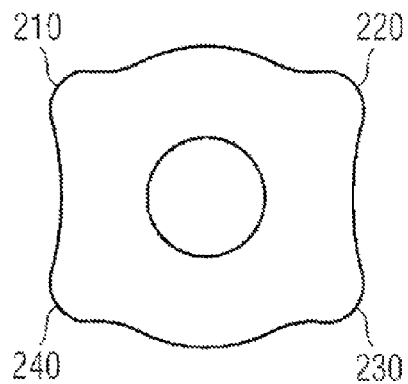
Figure 3A:
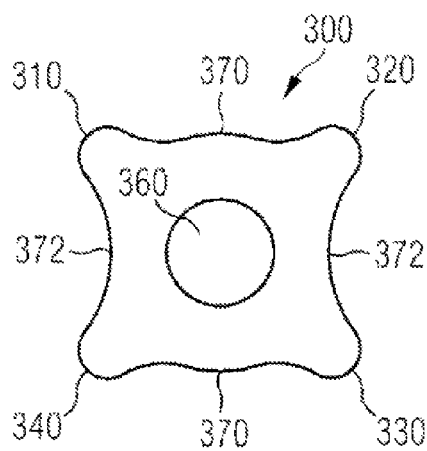
Figure 3B:
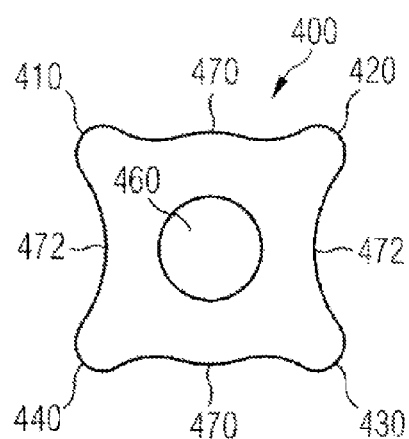
Figure 4:
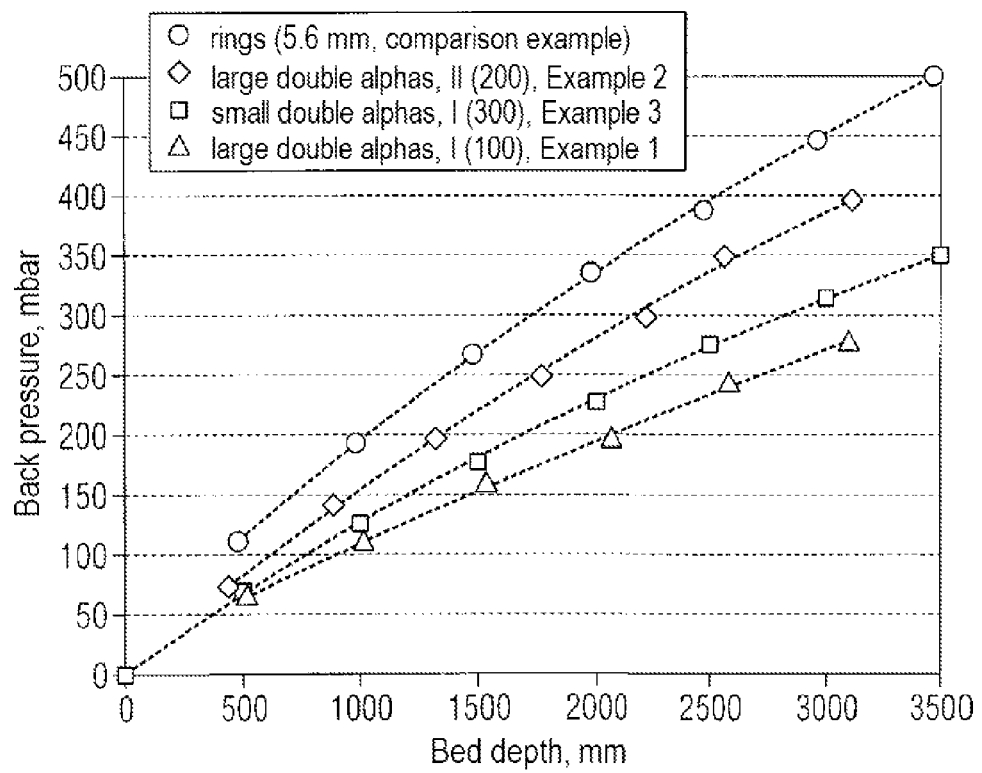

All non-mutually exclusive features described here of embodiments can be combined with one another. Identical elements of the embodiments are given identical reference numbers in the following description. The dimensions and angles of embodiments and examples described here can be understood to allow for customary measuring and manufacturing tolerances. Elements of one embodiment can be used in the other embodiments without further mention. Embodiments of the invention will now be described in more detail in the following examples with reference to figures, without being regarded as limiting. There are shown in:

FIGS. 1a and 1b a shaped catalyst body according to a first example;

FIGS. 2a and 2b a shaped catalyst body according to a second example;

FIGS. 3a and 3b shaped catalyst bodies according to a third and fourth example; and FIG. 4 the behaviour under pressure of the first to third examples compared with a comparison example.

FIGS. 1a and 1b show a shaped catalyst body 100 according to a first example (Example 1) of an embodiment. The shaped catalyst body is formed as cylinder with a base 150, a cylinder surface 152, a cylinder axis 154 and at least one continuous opening 160 running parallel to the cylinder axis. A geometric base body enclosing the shaped catalyst body 100 is a prism 10 with a hexagonal base 11, as shown in FIG. 1b. A prism with a four-sided base (not shown), e.g. a cuboid, can be selected as an alternative geometric shaped body enclosing the shaped catalyst body.

FIG. 1a shows a perspective view of the shaped catalyst body 100, while FIG. 1b shows a top view of the base 150 of the shaped catalyst body as well as of the base 11 of the prism 10. The cylinder and also the base 150 of the cylinder have four rounded corners 110, 120, 130 and 140, i.e. lobes which extend along the cylinder parallel to the cylinder axis. The lobes 110 and 120 or 130 and 140 together each form a long side 156 of the base 150. The lobes 120 and 130 or 140 and 110 together each form a broad side 158 of the base 150. The dimensions of the long sides 156 are greater than the dimensions of the broad sides 158. The long side 156 measures 7.2 mm, the broad side 158 measures 5.5 mm.

The four lobes 110, 120, 130, 140 each have the same external diameter of 1.5 mm, i.e. the radius of the respective circular arc formed by the lobes is 0.75 mm. A protrusion 170 is provided between the lobes on each of the long sides 156, while there are recesses 172 between the lobes on the broad sides 158. The shaped catalyst body 100 can therefore be described as a double alpha. It is designed as ring or hollow cylinder, wherein the lobes serve as spacers. The external diameter of the cylinders, i.e. the distance between the recesses 172, is 6 mm. The diameter of the opening 160 is 2.4 mm.

The corners 110 to 140 each have a centre of gravity 180, wherein the centre of gravity is in each case 3.5 mm from the cylinder axis.

The position of the rounded corners or lobes 110 to 140 is defined by an angle. The corners 110 to 140 are arranged in the base such that the angle between the perpendicular on a straight line through the centres of gravity of the corners 120 and 130 or 140 and 110 that define the width of the prism base and a straight line through the centre of gravity of these corners and through the cylinder axis is 35°.

The length of the lobes is defined by the distance from the cylinder axis to the centre of gravity of the lobes, which is 3.5 mm in this example.

The radii of the circular arcs formed by the protrusions 170 are 6 mm in each case and the radii of the circular arcs formed by the recesses 172 are 3 mm in each case. The radii of the recesses formed between the corners 110 to 140 and the protrusions 170, i.e. their circular arcs, are each 1.8 mm. The protrusions 170 can be understood as two further corners of the shaped catalyst body 100 which are different from the corners 110 to 140.

The height, i.e. the length parallel to the cylinder axis 154, of the shaped catalyst body 100 is 6 mm. The surrounding geometric shape is the prism 10 the length of the cross-section of which is greater than its width.

The hexagonal base of the prism 10 enclosing the shaped catalyst body 100 is spanned in the present example by the corners 110 to 140 and the protrusions 170. Alternatively, as mentioned above, in Example 1 the prism enclosing the shaped body 100 can be a cuboid with a rectangular base, the short side of which is defined by the protrusions 170 and the long side of which is defined by the corners 110 and 120 or 130 and 140.

FIGS. 2a and 2b show a shaped catalyst body 200 according to a second example (Example 2) of an embodiment. The shaped body 200 differs from the shaped body 100 in the length of the lobes 210, 220, 230, 240, which is 3 mm in this example.

FIGS. 3a and 3b illustrate the shaped catalyst bodies 300 and 400 as a third and fourth example (Examples 3 and 4) of an embodiment. The shaped catalyst bodies 300 and 400 of these examples are designed smaller than the shaped bodies 100 and 200, with the following dimensions: the height, i.e. the dimension of the shaped catalyst body parallel to the cylinder axis, is 5.5 mm. The diameter of the opening 360 or 460 is 2.4 mm. The length of the lobes 310 to 340 or 410 to 440 is 3.5 mm. The long sides of the base measure 6.67 mm. The broad sides of the base measure 5.9 mm. The angle defining the position of the lobes is in each case 40°. The diameter of the lobes 310 to 340 and 410 to 440 is 1.4 mm. The recesses 372 and 472 are limited by circular arcs with a radius of 4 mm. The protrusions 370 and 470 form circular arcs each with a radius of 2.75 mm. The radii of the recesses formed between the corners 310 to 340 and the protrusions 370 or 470 are 2.5 mm for the third example, shaped body 300 (FIG. 3a), and 1.5 mm for the fourth example, shaped body 400 (FIG. 3b).

In Examples 3 and 4, the prism enclosing the respective shaped body 300 or 400 is a cuboid with a rectangular base (not shown), which is spanned by the four corners of the respective shaped body.

According to the invention, the radius of the circular arc formed in each case by the rounded corners 110 to 140, 210 to 240, 310 to 340 and 410 to 440 can be in the range of from 0.5 to 2.5 mm. According to the invention, the radius of the circular arc formed in each case by the rounded protrusions 170, 270, 370 and 470 can be in the range of from 2 to 3.5 mm. Furthermore, according to the invention, the radius of the circular arc formed in each case by the rounded recesses 172, 272, 372 and 472 can be in the range of from 1 to 9 mm.

A comparison example consists of a ring with a diameter of 5.6 mm, a dimension (height) along the ring axis of 5.6 mm and a hole diameter of 2.4 mm.

Examples 1 to 3 as well as the comparison example consisted of vanadium phosphorus mixed oxide (VPO, molar ratio P/V=1.07; carbon content of the shaped body 4.2 wt. %; oxidation number vanadium $VO_x$ 4.2; BET surface area of the shaped body 22 $m^2/g$, measured according to DIN 66131). Additional examples 1a, 2a, 3a, and a comparison example a were shaped according to the shaped bodies of Examples 1 to 3 as well as of the comparison example and consisted of an $Al_2O_3/SiO_2$ mixed oxide ($Al_2O_3/SiO_2$=90/10, manufacturer: Sasol, BET surface area: 400 $m^2/g$, pore volume: 0.75 ml/g). Further examples, not described here in more detail, were shaped bodies of $SiO_2$, $TiO_2$ and $ZrO_2$, which were shaped like the shaped bodies of Examples 1 to 3 as well as of the comparison example.

The pressing forces occurring during the tabletting of Examples 1 to 3 and of the comparison example in a Kg-pharma carousel-type tablet press RoTabT are reproduced in Table 1. The pressing and ejection forces listed in Table 1 were read from the tablet press.

TABLE 1

| Sample | Rings, comparison example | Large double alphas, I (100), Example 1 | Large double alphas, II (200), Example 2 | Small double alphas, I (300), Example 3 |
|---|---|---|---|---|
| Pressing force, kN | 9.0-9.8 | 3.8-4.3 | 4.0-4.5 | 2.0-2.2 |
| Ejection force, N | 750-800 | 340-380 | 350-400 | 280-320 |

If high pressing forces need to be used in order to be able to produce shaped catalyst bodies in the shape of tablets with the required stability (lateral compressive strength), and high ejection forces (=friction when ejecting the tablets) are at work, the tabletting tools, i.e. punches and female moulds, experience strong mechanical stresses. The greater the mechanical stress, the greater the wear on the tools, which shortens the life of the tools. With the shapes according to the invention, lower pressing and ejection forces occur than with the rings, in particular in the case of shaped body 300.

The improved pressure-loss behaviour of feedstocks of the shaped bodies 100, 200 and 300 compared with a feedstock of the ring from the comparison example is shown in FIG. 4. The measurements were carried out at room temperature and the volume flow was 4 $m^3/h$ (standard conditions). In order to quantify the pressure-loss behaviour, the back pressure was measured in a 4 m-long tube with an internal diameter of 21 mm relative to the bed depth. In a series of tests, the shaped bodies of Examples 1 to 3 as well as of the comparison example of vanadium phosphorus mixed oxide (VPO) were used. Another series of tests related to Examples 1a, 2a, 3a, and comparison example a which were formed according to the shaped bodies of Examples 1 to 3 as well as the comparison example, but consisted of the $Al_2O_3/SiO_2$ mixed oxide.

The resulting back pressure of the series of tests of Examples 1 to 3 as well as of the comparison example is plotted as a function of the bed depth in FIG. 4. FIG. 4 shows that the pressure loss when using a feedstock of Example 1, a feedstock of Example 2 and a feedstock of Example 3 was much smaller than when using a feedstock of the comparison example. The series of tests of Examples 1a, 2a, 3a, and of the comparison example a is not shown in FIG. 4, as it led to results identical to those in the series of tests of Examples 1 to 3 as well as the comparison example. It was thus shown that there is no difference in behaviour under back pressure when shaped bodies are produced from VPO or $Al_2O_3$. Any differences in the surface roughness are of little or no importance.

Tables 2 and 3 show the results of the performance measurements for two different GHSVs. The length of the feedstock was in each case 5.5 m in the reactor with an internal diameter of the tube of 21 mm. In each case, 2650 mbar (absolute) was set as reactor inlet pressure. A GHSV of 1810 $h^{-1}$ was used for the measurements of Table 2 and a GHSV of 2015 $h^{-1}$ for the measurements of Table 3.

TABLE 2

Length of the feedstock: 5.5 m; tube diameter: 21 mm; reactor inlet pressure: 2650 mbar (absolute); GHSV: 1810 $h^{-1}$

| Conditions/ Results | Rings, comparison example | Large double alphas, Example 1 | Large double alphas, Example 2 | Small double alphas, Example 3 |
|---|---|---|---|---|
| Salt bath temperature, ° C. | 420 | 415 | 419 | 421 |
| Hot spot temperature, ° C. | 457 | 443 | 453 | 449 |
| Conversion, mol.-% | 85.5 | 86.5 | 85.0 | 85.5 |
| Selectivity, mol.-% | 68.5 | 67.1 | 68.9 | 71.0 |
| Pressure loss, mbar | 800 | 515 | 590 | 550 |
| MA productivity, $g_{MA}/(kg_{cat} \cdot h)$ | 115 | 128 | 118 | 147 |
| Productivity/ Pressure loss, $g_{MA}/(kg_{cat} \cdot h \cdot mbar)$ | 0.144 | 0.249 | 0.198 | 0.267 |

TABLE 3

Length of the feedstock: 5.5 m; tube diameter: 21 mm; reactor inlet pressure: 2650 mbar (absolute); GHSV: 2015 h$^{-1}$

| Conditions/Results | Rings, comparison example | Large double alphas, Example 1 | Large double alphas, Example 2 | Small double alphas Example 3 |
|---|---|---|---|---|
| Salt bath temperature, ° C. | 421 | 416 | 419 | 423 |
| Hot spot temperature, ° C. | 453 | 443 | 448 | 445 |
| Conversion, mol.-% | 83 | 82 | 82 | 82 |
| Selectivity, mol.-% | 69.9 | 67.9 | 69.4 | 71.3 |
| Pressure loss, mbar | 990 | 650 | 740 | 690 |
| MA productivity, $g_{MA}/(kg_{cat} \cdot h)$ | 124 | 137 | 126 | 157 |
| Productivity/Pressure loss, $g_{MA}/(kg_{cat} \cdot h \cdot mbar)$ | 0.125 | 0.211 | 0.170 | 0.228 |

As can be seen from Tables 2 and 3, higher productivities are obtained with the shaped catalyst bodies 100, 200 and 300 of Examples 1 to 3 than with the ring geometries of the comparison example, with comparable yields of butane and comparable salt bath temperatures. The improvement achieved by the catalyst shapes of Examples 1 to 3 compared with the comparison example is shown particularly clearly with the help of the quotient of productivity and pressure loss (=productivity per expenditure of energy). The following order results for the quotient: Example 3>Example 1>Example 2>comparison example.

It is furthermore clear from Tables 2 and 3 that the maximum temperature in the catalyst bed (hot spot temperature) is lower with the shaped catalyst bodies 100, 200 and 300 of Examples 1 to 3 compared with the comparison example. This can be attributed to the fact that an improved heat removal and an improved heat distribution in the catalyst bed is achieved with the shaped catalyst bodies 100, 200 and 300 of Examples 1 to 3 compared with the comparison example. These effects are documented in Tables 2 and 3 by the temperature differences between the salt bath and the hot spot temperature of Examples 1 to 3, which are smaller compared with the difference between the salt bath temperature and the hot spot temperature of the comparison example.

TABLE 4

Characteristic data of the double alphas compared with characteristics of different rings

| Shaped boby | Bulk density[1] kg/l | Tablet density[2] kg/l | Average lateral compressive strength, N |
|---|---|---|---|
| Double alphas (100) Example 1 | 0.62 | 1.70 | 31, 223[3] |
| Double alphas (200) Example 2 | 0.69 | 1.71 | 34, 230[3] |
| Double alphas (300) Example 3 | 0.56 | 1.58 | 40, 106[3] |
| Rings, comparison example (Ø = 5.6 mm) | 0.76 | 1.75 | 24 |

[1] measured in the tube of length 1 m and internal diameter 21 mm
[2] measured via Hg porosimetry
[3] first region not very stable side, second region stable side Table 4 gives additional characteristic data for the shaped catalyst bodies 100, 200 and 300 of Examples 1 to 3 compared with data for rings of the comparison example. The bulk density was measured in the tube 1 m long and with an internal diameter of 21 mm based on DIN ISO 697. The differences in the measurement method used compared with the method according to DIN ISO 697 were the measurement volume, obtained through the length of 1 m of the tube and the internal diameter of 21 mm, and the use of shaped bodies instead of powder. The tablet density was measured by means of Hg porosimetry (Porotec, Pascal440 series), according to DIN 66133. The lateral compressive strength measurement was carried out with a tablet tester (Pharmatron, Dr. Schleuniger, model 6D), according to ASTM D4179-88a. It is shown that, compared with rings, the so-called double alphas, in addition to a lower pressure-loss behaviour in the fixed bed, have a lower bulk density, a lower tablet density and a higher mechanical stability, actually 5-10 times higher, in the spatial direction of the longer side of the base.

The invention claimed is:

1. A shaped catalyst body for the catalytic conversion of organic and inorganic compounds in fixed-bed reactors, wherein the shaped catalyst body (100; 200; 300; 400) has the form of a cylinder with a base (150), a cylinder surface (152), a cylinder axis (154) and at least one continuous opening (160) running parallel to the cylinder axis, and the base of the cylinder has at least four lobes (110, 120, 130, 140; 210; 220, 230, 240; 310, 320, 330, 340; 410, 420, 430, 440), and has a geometric surface area and a volume, wherein the ratio of the geometric surface area of the shaped catalyst body to the volume of the shaped catalyst body is in the range from 1 to 1.8 mm$^{-1}$.

2. The shaped catalyst body according to claim 1, wherein a geometric base body enclosing the shaped catalyst body is a prism (10) which has a prism base with a length and a width, wherein the length is greater than the width.

3. The shaped catalyst body according to claim 2, wherein the prism (10) is a cuboid; and/or
wherein the ratio of the volume of the shaped catalyst body to the volume of the surrounding cuboid is greater than 80% without taking the at least one opening into account and greater than 70% taking the at least one opening into account; and/or
wherein the lobes are enclosed by prism corners of the prism base; and/or
wherein two lobes define the length of he prism base and/or two lobes define the width of the prism base.

4. The shaped catalyst body according to claim 2, wherein the dimension or height of the shaped catalyst body parallel to the cylinder axis is in the range from 2 mm to 20 mm and/or the length of the prism base is in the range from 2 mm to 10 mm.

5. The shaped catalyst body according to claim 4, wherein the dimension or height of the shaped catalyst body parallel to the cylinder axis is in the range from 3 mm to 6 mm.

6. The shaped catalyst body according to claim 4, wherein the length of the prism base is in the range from 4 mm to 8 mm.

7. The shaped catalyst body according to claim 1, wherein a recess (172) is provided in the cylinder surface between two adjacent lobes, and/or a protrusion (170) is provided in the cylinder surface between two adjacent lobes.

8. The shaped catalyst body according to claim 7, wherein the protrusion is provided between lobes that define the length, and/or the recess provided between lobes that define the width.

9. The shaped catalyst body according to claim 7, wherein the external diameter of the cylinder or the distance between two opposite recesses is in the range from 3 mm to 10 mm; and/or
the diameter of the opening is in the range from 0.5 mm to 4 mm.

10. The shaped catalyst body according to claim 9, wherein the external diameter of the cylinder or the distance between two opposite recesses is in the range from 5 mm to 8 mm.

11. The shaped catalyst body according to claim 9, wherein the diameter of the opening is in the range from 1 mm to 3 mm.

12. The shaped catalyst body according to claim 1, wherein the shaped catalyst body has four lobes; and/or
wherein the shaped catalyst body has two recesses arranged opposite each other and/or two protrusions arranged opposite each other.

13. The shaped catalyst body according to claim 12, wherein at least one element selected from the recesses, and the protrusions is rounded.

14. The shaped catalyst body according to claim 12, wherein each of the protrusions has a rounded shape in the form of a circular arc, wherein the radius of the circular arc formed by the protrusions is in the range from 2 mm to 3.5 mm and/or
wherein each of the recesses has a rounded shape in the form of a circular arc,
wherein the radius of the circular arc formed by the recesses is in the range of from 1 mm to 9 mm.

15. The shaped catalyst body according to claim 1, wherein the each of the lobes has a center of gravity (180), wherein the distance between the center of gravity of each lobe and the cylinder axis is in the range from 1.5 mm to 5 mm and/or at least two of the lobes are different from each other and/or
the lobes have a rounded shape, wherein the rounded shape has a diameter in the range from 1 to 2 mm and/or
the lobes have a rounded shape in the form of a circular arc, wherein the radius of the circular arc is in the range of from 0.5 to 2.5 mm.

16. The shaped catalyst body according to claim 15, wherein the lobes are arranged in the base such that the angle between the perpendicular on a straight line through the centers of gravity of two lobes that define the width of a prism base and a straight, line through the center of gravity of these lobes and through the cylinder axis is in the range from 10° to 75°.

17. The shaped catalyst body according to claim 16, wherein the lobes are arranged in the base such that the angle between the perpendicular on a straight line through the centers of gravity of two lobes that define the width of a prism base and a straight line through the center of gravity of these lobes and through the cylinder axis is in the range from 25° to 60°.

18. The shaped catalyst body according to claim 15, wherein the distance between the center of gravity of each lobe and the cylinder axis is in the range from 2.5 mm to 4 mm.

19. The shaped catalyst body according to claim 1, wherein the bulk density of the shaped catalyst body is less than 0.75 kg/l and/or
an average unidirectional lateral compressive strength is greater than 28 N and/or a different average unidirectional lateral compressive strength is greater than 70 N.

20. The shaped catalyst body according to claim 1, comprising
at least one element selected from mixed oxides of vanadium and phosphorus, one or more metals of the sub-groups of the periodic table, a metal oxide or a mixed metal oxide of metals of the sub-groups of the periodic table, and one or more noble metals.

21. The shaped catalyst body according to claim 1, comprising at least one element selected from aluminium oxide, silicon dioxide, aluminium silicate, zirconium dioxide, and titanium dioxide.

* * * * *